(12) United States Patent
Swift (10) Patent No.: US 9,345,623 B2
(45) Date of Patent: May 24, 2016

(54) SURGICAL MESH SPRAY AND DELIVERY SYSTEM

(71) Applicant: Biomet Biologics, LLC, Warsaw, IN (US)

(72) Inventor: Matthew Swift, Fort Wayne, IN (US)

(73) Assignee: BIOMET BIOLOGICS, LLC, Warsaw, IN (US)

(*) Notice: Subject to any disclaimer, the term of this patent is extended or adjusted under 35 U.S.C. 154(b) by 59 days.

(21) Appl. No.: 14/330,778

(22) Filed: Jul. 14, 2014

(65) Prior Publication Data

US 2014/0322430 A1    Oct. 30, 2014

Related U.S. Application Data

(62) Division of application No. 13/206,190, filed on Aug. 9, 2011, now Pat. No. 8,776,716.

(51) Int. Cl.
*B05C 5/00* (2006.01)
*A23G 3/26* (2006.01)
*A61F 13/00* (2006.01)
*B05B 7/08* (2006.01)
*B05B 15/04* (2006.01)
*A61F 2/00* (2006.01)

(52) U.S. Cl.
CPC ......... *A61F 13/00991* (2013.01); *A61F 2/0063* (2013.01); *B05B 7/08* (2013.01); *B05B 15/04* (2013.01)

(58) Field of Classification Search
CPC ...... A61L 27/34; A61L 27/225; A61L 27/227
USPC .......................... 427/2.24, 2.31; 424/423, 424
See application file for complete search history.

(56) References Cited

U.S. PATENT DOCUMENTS

| 2,561,392 | A | | 7/1951 | Marshall |
| 2,799,241 | A | | 7/1957 | Wurster |
| 3,903,839 | A | | 9/1975 | Rowe et al. |
| 4,307,717 | A | | 12/1981 | Hymes et al. |
| 4,751,133 | A | | 6/1988 | Szycher et al. |
| 5,156,589 | A | | 10/1992 | Langen et al. |
| 5,582,596 | A | * | 12/1996 | Fukunaga ........ A61B 17/00491 222/137 |
| 5,997,517 | A | | 12/1999 | Whitbourne |
| 6,368,658 | B1 | * | 4/2002 | Schwarz ................. A61L 27/28 427/2.15 |
| 6,462,018 | B1 | * | 10/2002 | Cederholm-Williams ............. A61L 24/106 424/423 |
| 6,673,453 | B2 | | 1/2004 | Beavers et al. |
| 6,746,869 | B2 | | 6/2004 | Pui et al. |

(Continued)

FOREIGN PATENT DOCUMENTS

WO    WO-9735533 A1    10/1997

*Primary Examiner* — Cachet Sellman
(74) *Attorney, Agent, or Firm* — Schwegman Lundberg & Woessner P.A.

(57) ABSTRACT

A device for spraying a biological substance onto a biocompatible implant. The device includes a housing that defines a sterile chamber. A spray head is within the chamber and proximate to a first end. A first conduit is configured to direct the biological substance into the chamber through a first spray tip of the spray head. A second conduit is configured to direct an activator into the chamber through a second spray tip of the spray head. A third conduit is configured to direct compressed air to the chamber through a third spray tip of the spay head. The spray head is configured to direct a coating of the biological substance as activated by the activator to the implant seated within the chamber at a second end that is opposite to the first end.

19 Claims, 5 Drawing Sheets

(56) References Cited

U.S. PATENT DOCUMENTS

| | | | |
|---|---|---|---|
| 6,818,063 B1 * | 11/2004 | Kerrigan | B05C 13/025 118/500 |
| 6,981,944 B2 | 1/2006 | Jamiolkowski et al. | |
| 7,335,391 B1 * | 2/2008 | Pacetti | A61L 31/10 427/2.1 |
| 7,709,048 B2 | 5/2010 | Teichman et al. | |
| 7,858,143 B2 * | 12/2010 | Hossainy | B05B 13/0235 118/500 |
| 8,776,716 B2 | 7/2014 | Swift | |
| 2004/0006296 A1 | 1/2004 | Fischell et al. | |
| 2004/0234576 A1 | 11/2004 | Martin et al. | |
| 2006/0273050 A1 * | 12/2006 | Higgins | B01D 21/262 210/787 |
| 2008/0109017 A1 | 5/2008 | Herweck et al. | |
| 2008/0118550 A1 | 5/2008 | Martakos et al. | |
| 2008/0193424 A1 * | 8/2008 | McKale | A61K 35/16 424/93.7 |
| 2009/0192528 A1 | 7/2009 | Higgins et al. | |
| 2010/0076464 A1 * | 3/2010 | Sheetrit | A61L 31/10 606/151 |
| 2011/0020531 A1 * | 1/2011 | Larson | A61F 2/0077 427/2.24 |
| 2011/0177150 A1 * | 7/2011 | Pathak | A61K 35/12 424/422 |
| 2013/0040042 A1 | 2/2013 | Swift | |

\* cited by examiner

SURGICAL MESH SPRAY AND DELIVERY SYSTEM

CROSS-REFERENCE TO RELATED APPLICATIONS

This application is a divisional of U.S. patent application Ser. No. 13/206,190 filed on Aug. 9, 2011. The entire disclosure of the above application is incorporated herein by reference.

FIELD

The present disclosure relates to devices and methods for spraying a biological substance onto a biocompatible implant, such as a surgical mesh implant.

BACKGROUND

This section provides background information related to the present disclosure, which is not necessarily prior art.

A surgical mesh implant can be used to reinforce a soft tissue defect repair site. Prior to implantation, the surgical mesh may be coated with a combination of autologous and/or allogenic fluidic tissues. It is desirable to coat the mesh implant evenly and efficiently, without wasting the fluidic tissues.

SUMMARY

This section provides a general summary of the disclosure, and is not a comprehensive disclosure of its full scope or all of its features.

The present teachings provide for a device for sterilely spraying a biological substance onto a biocompatible implant. The device includes a housing, a sidewall, a spray head, a first conduit, a second conduit, and a third conduit. The housing defines a sterile chamber having a first end and a second end that is opposite to the first end. The sidewall extends between the first end and the second end. The spray head is within the chamber and proximate to the first end. The first conduit extends through the first end to the spray head, the first conduit is configured to direct the biological substance to the chamber through a first spray tip of the spray head. The second conduit extends through the first end to the spray head and is configured to direct an activator of the biological substance to the chamber through a second spray tip of the spray head. The third conduit extends through the first end to the spray head. The third conduit is configured to direct compressed air to the chamber through a third spray tip of the spay head and contact both the biological substance and the activator as each enters the chamber. The spray head is configured to direct a coating of the biological substance as activated by the activator to the implant seated within the chamber proximate to the second end.

The present teachings further provide for a housing, a spray head, a first conduit, a second conduit, a third conduit, a mesh implant, and a separation device. The housing defines a chamber having a first end, a second end, and a sidewall extending between the first end and the second end. The spray head is within the chamber. The first conduit extends from the spray head to an exterior of the chamber. The first conduit is associated with a first connector configured to mate with a first syringe that includes a first component of the biological substance. The second conduit extends from the spray head to the exterior of the chamber. The second conduit is associated with a second connector configured to mate with a second syringe including a second component of the biological substance. The third conduit extends from the spray head to the exterior of the chamber. The third conduit is associated with a third connector configured to mate with a compressed air source. The mesh implant is seated within the chamber proximate to the second end of the chamber. The separation device is between the first end and the mesh implant and is operable to separate the chamber into a first portion and a second portion. The first portion includes the first end of the chamber and the spray head. The second portion includes the second end of the chamber and the mesh implant. The first conduit, the second conduit, and the third conduit are spaced apart such that when the first conduit includes the first component, the second conduit includes the second component, and the third conduit includes compressed air, the first component, the second component, and the compressed air remain separated until entering the chamber.

The present teachings also provide for a method for sterilely spraying a biological substance onto a mesh implant that includes the following: connecting a first syringe including the biological substance to a first connector proximate to a first conduit that extends to a first spray tip of a spray head mounted within a housing, the housing defining a chamber having a first end, a second end, and a sidewall extending between the first end and the second end; connecting a second syringe including an activator of the biological substance to a second connector at a second conduit that extends to a second spray tip of the spray head that is spaced apart from the first spray tip; connecting an air compressor line to a third connector at a third conduit that extends to a third spray tip of the spray head that is spaced apart from both the first spray tip and the second spray tip, and activating an air compressor to introduce compressed air into the housing through the third spray tip; simultaneously compressing the first syringe including the biological substance and the second syringe including the activator to introduce the biological substance into the housing through a second spray tip of the spray head and to introduce the activator into the housing through the second spray tip, the biological substance is activated by the activator upon entering the chamber; and coating the mesh implant seated within the housing with the activated biological substance, which is provided as a spray upon being exposed to the compressed air at the spray head.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
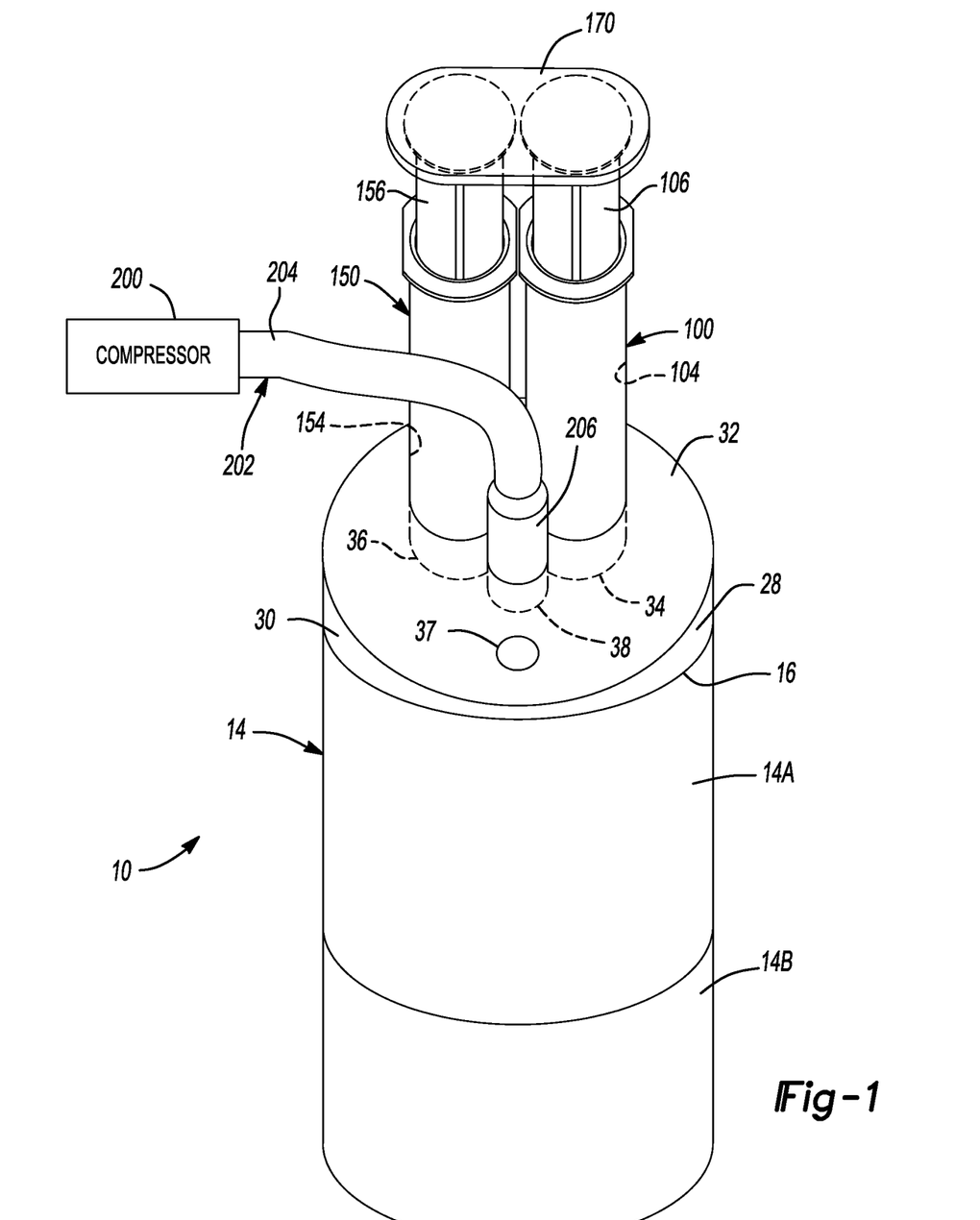
FIG. 1 is perspective view of a device for spraying a biological substance onto a biocompatible implant according to the present teachings, a compressor and syringes are connected to the device.

With initial reference to FIGS. 1-4, a device 10 for sterilely spraying a biological substance onto a biocompatible implant, such as a surgical mesh 12, is illustrated. The device 10 includes a housing 14. The housing 14 includes a first end wall 16, a second end wall 18 opposite to the first end wall 16, and at least one sidewall 20 that extends between the first end wall 16 and the second end wall 18 to define a chamber 22. The sidewall 20 can be round or circular (as illustrated in FIG. 1) to provide the chamber 22 with a cylindrical shape. The sidewall 20 can also include multiple planar surfaces, such as four, to provide the chamber 22 with a square shape. The chamber 22 includes a first end 24 proximate to the first end wall 16 and a second end 26 proximate to the second end wall 18.

A connector base 28 is at a side of the first end wall 16 opposite to the chamber 22. The connector base 28 includes a body portion 30 and a superior surface 32. The superior surface 32 may be angled or slanted with respect to the first end wall 16, as illustrated in FIGS. 1-4. The superior surface 32 can also be planar with respect to the first end wall 16 such that the superior surface 32 and the first end wall 16 lie in spaced apart, parallel planes. Orienting the surface 32 as a slanted surface can facilitate access to connectors and conduits extending there through, as described in detail herein.

Figure 3:
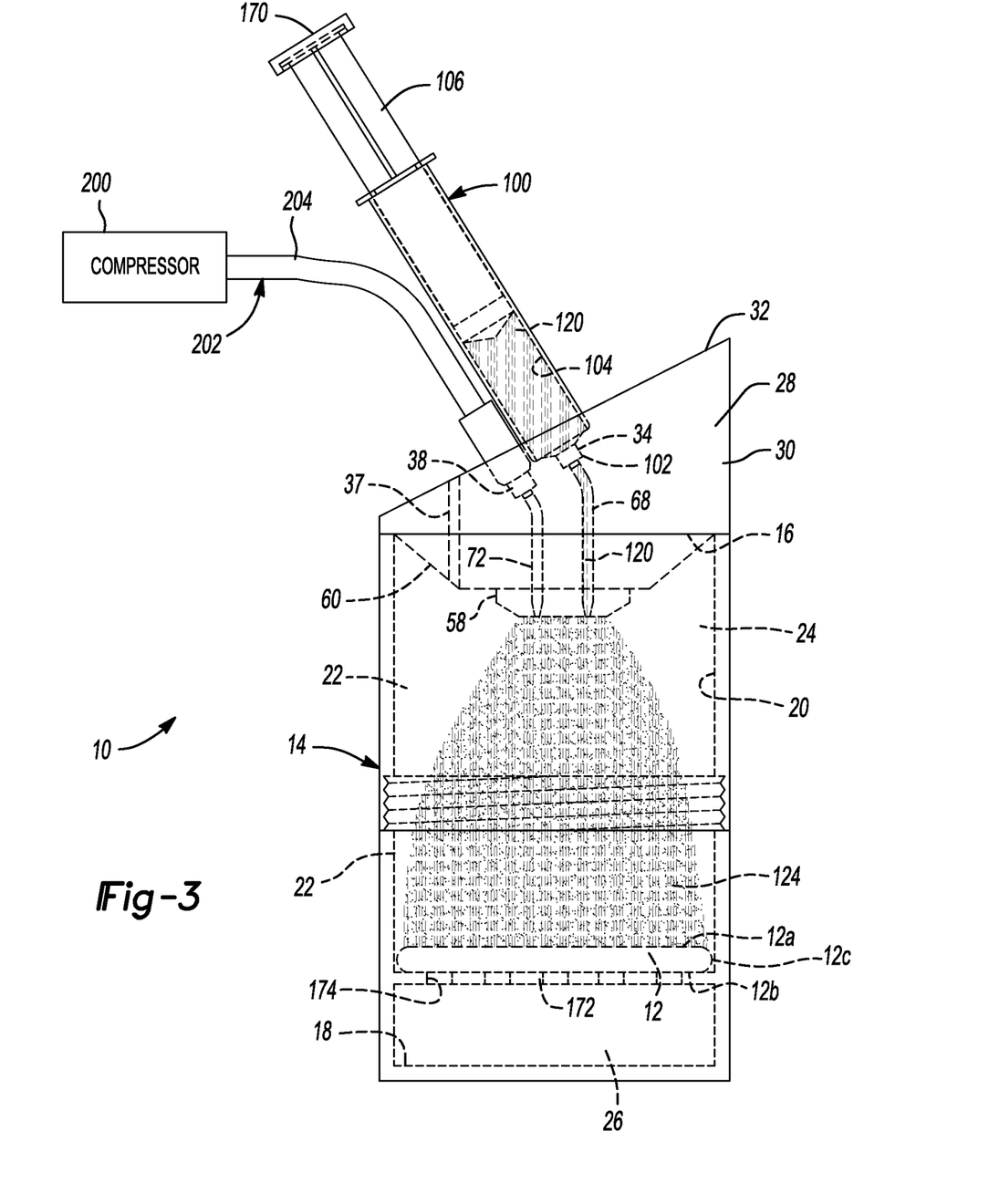
FIG. 3 is a side cross-sectional view of the device of FIG. 1.
Figure 4:
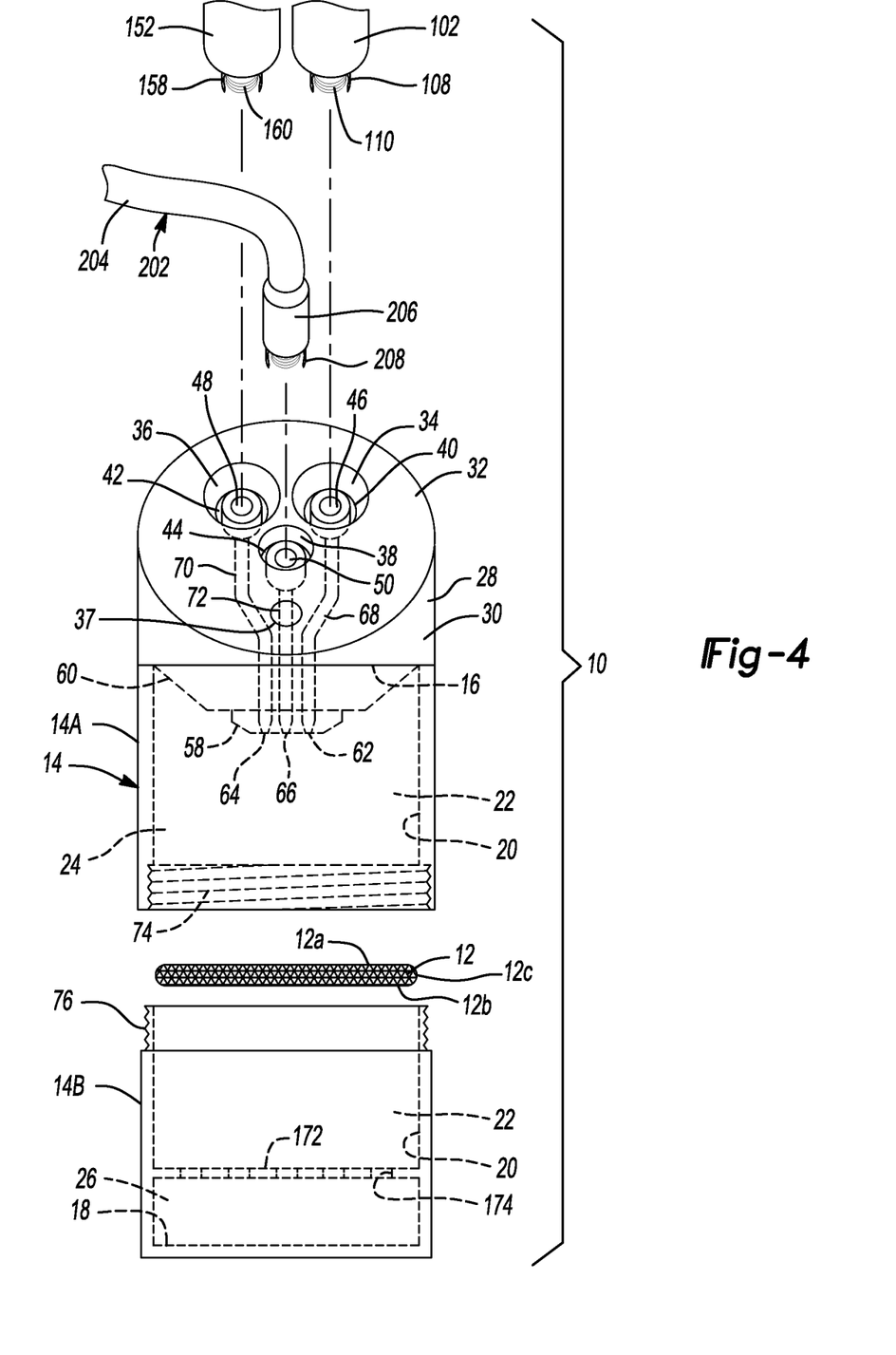
FIG. 4 is an exploded view of the device of FIG. 1.
Figure 5:
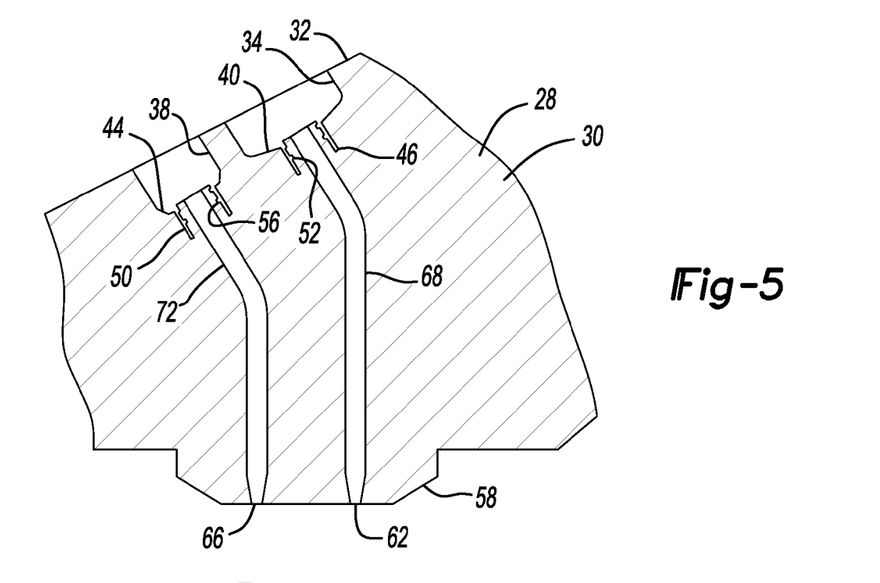
FIG. 5 is a cross-sectional view of a connector base of the device of FIG. 1.
Figures 6, 7:
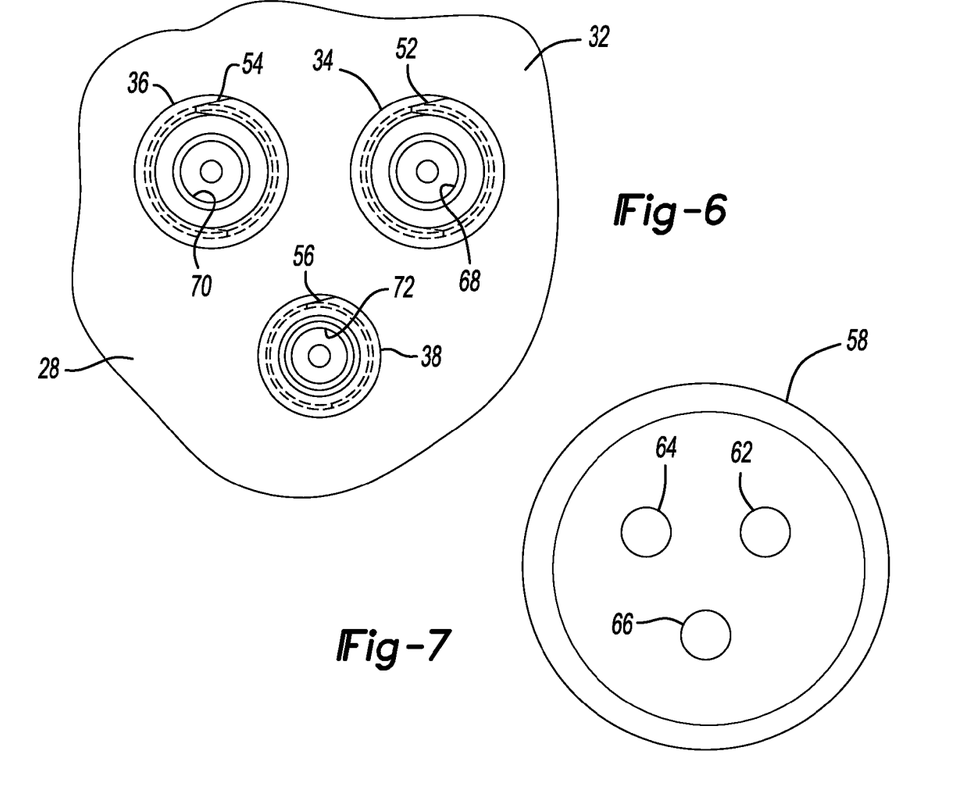
FIG. 6 is a plan view of the connector base of the device of FIG. 1.
FIG. 7 is a plan view of a spray head of the device of FIG. 1.

With continued reference to FIGS. 1-4 and additional reference to FIGS. 5 and 6, the connector base 28 includes a plurality of connectors, such as a first connector 34, a second connector 36, and a third connector 38. The first, second, and third connectors 34, 36, and 38 can be recessed within the connector base 28 beneath the superior surface 32, as illustrated, or may protrude from the superior surface 32. The first, second, and third connectors 34, 36, and 38, can be any suitable type of interlocking connector configured to cooperate with devices, such as syringes and an air compressor line, as described herein. For example, the first, second, and third connectors 34, 36, and 38 can be luer lock connectors, as illustrated. The first, second, and third connectors 34, 36, and 38 can be spaced apart at the superior surface 32 of the connector base 28 as illustrated; can be at any other suitable position on the connector base 28, such as at a side surface thereof; or can be at any other suitable location of the housing 14.

A vent 37 is included in the superior surface 32 and extends through the connector base 28 to the chamber 22. The vent 37 provides communication between the chamber 22 and the outer atmosphere to permit release of pressure from within the chamber 22 when compressed air is introduced to the chamber 22 as described herein.

The first, second, and third connectors 34, 36, and 38 respectively include a first recessed portion 40, a second recessed portion 42, and a third recessed portion 44, as illustrated in FIGS. 3 and 4 for example. At a center of the first recessed portion 40 is a first coupling device 46. At a center of the second recessed portion 42 is a second coupling device 48. At a center of the third recessed portion 44 is a third coupling device 50. The first, second, and third coupling devices 46, 48, and 50 can be any suitable types of coupling devices and can include, for example, first, second, and third ramped surfaces 52, 54, 56 respectively (FIGS. 5, 6), as typically included in a luer lock.

A spray head 58 is mounted within the chamber 22 proximate to the first end 24. The spray head 58 is mounted to a spray head base 60, which is mounted to the first end wall 16. With additional reference to FIG. 7, the spray head 58 includes a first spray tip 62, a second spray tip 64, and a third spray tip 66, which are spaced apart from each other. The spray tips 62, 64, and 66 can each include a nozzle that can be integral with the spray head 58 or modular to permit replacement of worn nozzles or use of nozzles of different shapes and sizes depending on the biological material and activator used in the device 10. The spray tips 62, 64, and 66 can be recessed within the spray head 58 or can extend from the spray head 58.

The first spray tip 62, the second spray tip 64, and the third spray tip 66 are each spaced apart and arranged in a triangular orientation. The spray tips 62, 64, and 66 can be spaced apart equidistant to each other, can be spaced apart at suitable varying distances, and can be arranged in any other suitable orientation in addition to the illustrated triangular orientation. The spray tips 62, 64, and 66 can include tapered portions to enhance the flow of material and air therefrom. The spray tips 62, 64, and 66 can each be parallel to one another, angled toward each other, or provided at any other suitable angle to facilitate flow of material and air therefrom.

With particular reference to FIGS. 2-5, a first conduit 68 extends between the first connector 34 and the first spray tip 62. A second conduit 70 extends between the second connector 36 and the second spray tip 64. A third conduit 72 extends between the third connector 38 and the third spray tip 66. The first, second, and third connectors 34, 36, and 38 are thus in fluid communication with the first spray tip 62, the second spray tip 64, and the third spray tip 66 respectively. The first conduit 68, the second conduit 70, and the third conduit 72 are each separate and distinct from each other, such that contents thereof are not mixed.

The first, second, and third conduits 68, 70, and 72 can each be any suitable device, opening, or formation suitable for respectively providing fluid communication between the first connector 34 and the first spray tip 62, between the second connector 36 and the second spray tip 64, and between the third connector 38 and the third spray tip 66. For example, the first, second, and third conduits 68, 70, and 72 can each include individual tubes or can each be distinct channels or bores defined within the connector base 28.

With particular reference to FIG. 4, the housing 14 includes a first portion 14A and a second portion 14B. The first portion 14A includes the first end wall 16 and the first end 24 of the chamber 22. The second portion 14B includes the second end wall 18 and the second end 26 of the chamber 22. The first portion 14A includes first female threads 74 and the second portion 14B includes second male threads 76. The first threads 74 are configured to cooperate with the second threads 76 to connect the first portion 14A to the second portion 14B. As illustrated in FIG. 4, the first portion 14A can be detached and separated from the second portion 14B to facilitate access to the chamber 22 and the surgical mesh 12 therein.

With reference to FIGS. 1-4 for example, a first syringe 100 generally includes a first syringe tip 102 (FIG. 3), a first syringe chamber 104, and a first plunger 106. The first syringe chamber 104 is in fluid communication with the first syringe tip 102. The first plunger 106 is slidably seated within the first syringe chamber 104 and operable to expel the contents of the first syringe chamber 104 through the first tip 102. The first tip 102 includes a first locking device 108 (FIG. 4), which is configured to interlock with the first connector 34. The first locking device 108 can thus be a luer lock with a first sloped surface 110 configured to cooperate with the first ramped surface 52 of the first connector 34.

The second syringe 150 is similar to the first syringe 100. The second syringe 150 generally includes a second syringe tip 152 (FIG. 4), a second syringe chamber 154, and a second plunger 156. The second syringe chamber 154 is in fluid communication with the second syringe tip 152. The second plunger 156 is slidably seated within the second syringe chamber 154 and operable to expel the contents of the second syringe chamber 154 through the second tip 152. The second tip 152 includes a second locking device 158 (FIG. 4), which is configured to interlock with the second connector 36. The second locking device 158 can thus be a luer lock with a second sloped surface 160 configured to cooperate with the second ramped surface 54 (FIG. 6) of the second connector 36. The first plunger 106 can be connected to the second plunger 156 with a coupling device 170. The coupling device 170 facilitates simultaneous actuation of the first and the second plungers 106 and 156.

Figure 2:
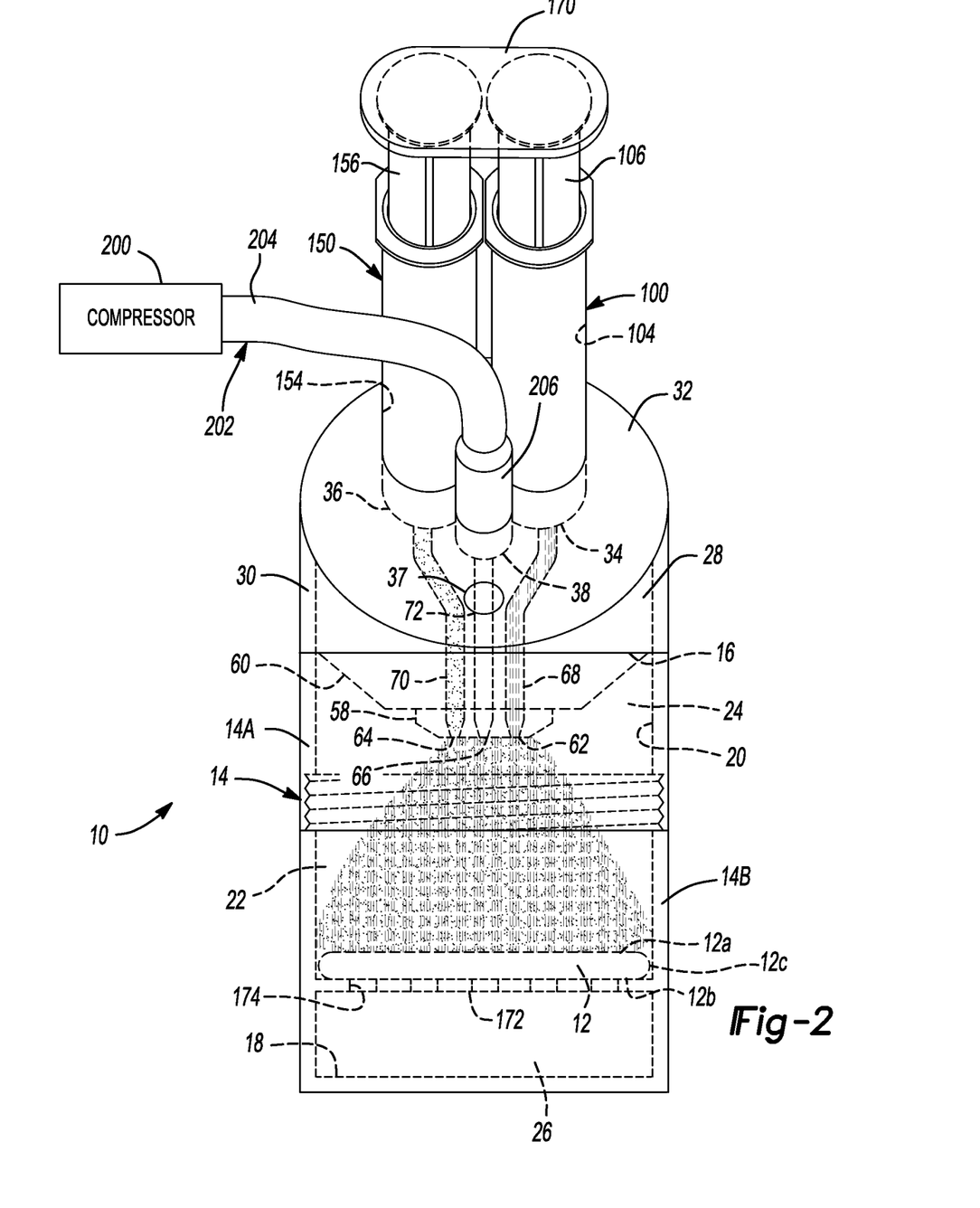
FIG. 2 is a partial cross-sectional view of the device of FIG. 1.

As illustrated in FIGS. 1-3, an air compressor 200 can be connected to the third connector 38 with an air line 202. The air compressor 200 can be any suitable source of compressed air or other suitable device to provide the contents of the first and the second syringes 100 and 150 in the form of a mist or spray upon exiting the spray head 58, as further described herein. The air line 202 can be any suitable device for directing air from the compressor 200 to the device 10, such as a flexible tube 204 including a third locking device 206 at and end thereof. The locking device 206 can be any suitable locking device, such as a luer lock or quick-connect including a third sloped surface 208 (FIG. 4) that is configured to cooperate with the third ramped surface 56 (FIG. 6) of the third connector 38 to connect the air line 202 to the device 10.

The surgical mesh 12 can be any suitable type of biocompatible implant to which it is desirable to evenly apply a biological substance. For example, the surgical mesh 12 can include TiMesh® (offered by Biomet of Warsaw, Ind.), a suitable acellular dermis, such as DermaSpan™ (offered by Biomet of Warsaw, Ind.), or a suitable xenograft. The mesh 12 can be seated on the end wall 18 or on a support surface 172 spaced apart from the end wall 18 at the second end 26.

The support surface 172 can define openings 174 to permit passage of activated biological material there through, or the support surface 172 can be a solid, impermeable surface. As described herein, when the surface 172 includes the openings 174, activated biological material applied to the surgical mesh 12 from the spray head 58 coats a first upper surface 12a of the mesh 12 facing the head 58 and coats interior portions of the mesh 12 as the biological material passes through the mesh 12. The biological material exits the mesh 12 at a second lower surface 12b, which is opposite to the first upper surface 12a. The biological material does not coat the second lower surface 12b, but rather passes through the openings 174 and is deposited at the end wall 18. When the support surface 172 does not include the openings 174, the biological material that passes through the mesh 12 settles between the support surface 172 and the second lower surface 12b and coats the second lower surface 12b of the mesh.

The device 10 can be used to apply various biological substances to an implant, such as the surgical mesh 12. For example, the first syringe chamber 104 of the first syringe 100 can include any suitable biological substance (autologous or allogeneic in origin) to be applied to the surgical mesh, such as the following: platelet rich plasma, platelet poor plasma, cryoprecipitate plasma, bone marrow aspirate, concentrated bone marrow aspirate, and a cell suspension sequestered from adipose tissue. The second syringe chamber 154 of the second syringe 150 can include any suitable activator for the biological substance of the first syringe chamber 104, such as the following activators of the coagulation cascade, which may be autologous, allogeneic, recombinant, or zenogeneic in origin: thrombin, batroxobin, Factor XII, Factor VII, Factor X, Factor V, Factor VIII, and Factor XIII. The activators may be delivered in any suitable solution, such as a calcium chloride solution.

In operation, the device 10 can be provided to the surgeon or hospital staff member with or without the surgical mesh 12 therein. The mesh 12 is provided sterile when included with the device 10. If the device 10 does not include the mesh 12, the housing 14 can be opened by uncoupling (such as by unscrewing) the first portion 14A from the second portion 14B to permit placement of the mesh 12 within the device 10. This can be done in a sterile environment to maintain the sterility of the mesh 12.

The first syringe 100 loaded with a selected biological substance 120 and the second syringe 150 loaded with a selected activator 122 for the biological substance 120 are then connected to the device 10 at the connector base 28. In particular, the first locking device 108 of the first syringe 100 is connected to the first coupling device 46 of the connector base 28. The second locking device 158 of the second syringe 150 is connected to the second coupling device 48 of the connector base 28. Also connected to the connector base 28 is the air line 202 of the air compressor 200, which is connected through cooperation between the third locking device 206 and the third coupling device 50.

The compressor 200 is activated to direct compressed air through the third conduit 72 and into the chamber 22 through the third spray tip 66 of the spray head 58. The vent 37 permits air to exit the chamber 22, and thus relieves the chamber 22 of excess pressure. The first and second plungers 106 and 156 are compressed to push the contents of the first and second syringe chambers 104 and 154 through the first conduit 68 and the second conduit 70 respectively and into the chamber 22 via the first spray tip 62 and the second spray tip 64 respectively of the spray head 58. Because the first, second, and third conduits 68, 70, and 72 are separate, the contents thereof are not mixed until the contents exit the spray head 58. This prevents the spray head 58 from being blocked or clogged by biological material that may otherwise be activated prior to exiting the spray head 58. As the biological substance 120 from the first syringe 100 exits the spray head 58 at the first spray tip 62, it is activated by the activator 122 of the second syringe 150, which simultaneously exits the spray head 58 at the second spray tip 64. The activated biological substance 124 is subject to compressed air exiting the third spray tip 66, which causes the activated biological substance 124 to be sprayed evenly onto the first upper surface 12a of surgical mesh 12. As the activated biological substance 124 passes through the mesh 12, interior fibers of the mesh 12 are coated. Portions of the activated biological substance 124 that contact the sidewall 20 of the chamber 22 may slide down the sidewall 20 to coat a side portion 12c of the surgical mesh 12. This maximizes the amount of biological substance 120 transferred from the first syringe 100 to the surgical mesh 12.

If the support surface 172 is solid and does not include the openings 174, the activated biological substance 124 that has passed through and around the mesh 12 settles between the support surface 172 and the second lower surface 12b of the mesh 12 to coat the second lower surface 12b of the mesh 12. If the support surface 172 includes the openings 174, the activated biological substance 124 that has passed through and around the mesh 12 passes through the openings 174 to the end wall 18, and thus the second lower surface 12b is not coated with the activated biological substance 124.

Application of the activated biological substance 124 to the surgical mesh 12 can be performed within the sterile field of an operating room, or in a non-sterile environment by non-sterile personnel with sterility of the mesh 12 being maintained due to the mesh 12 being housed within the chamber 22. After the activated biological substance 124 is applied to the surgical mesh 12, the syringes 100 and 150 and the compressor air line 202 can be disconnected from the device 10. If the activated biological substance 124 was applied to the surgical mesh 12 outside the sterile field by non-sterile personnel, the device 10 can be brought to a perimeter of the sterile field, opened by non-sterile personnel by unscrewing the first threads 74 of the first portion 14A from cooperation with the second threads 76 of the second portion 14B, and then the mesh 12 can be removed from the device 10 by sterile personnel in the sterile field. The surgical mesh 12 with the activated biological substance 124 evenly applied thereto can then be implanted at a suitable implantation site to facilitate healing.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for sterilely spraying a biological substance onto an implant comprising:
   connecting a first syringe including the biological substance to a first connector proximate to a first conduit that extends to a first spray tip of a spray head mounted within a housing, the housing defining a chamber having a first end, a second end, and a sidewall having a threaded portion, the sidewall extending between the first end and the second end;
   connecting a second syringe including an activator of the biological substance to a second connector at a second conduit that extends to a second spray tip of the spray head that is spaced apart from the first spray tip;
   connecting an air compressor line to a third connector at a third conduit that extends to a third spray tip of the spray head that is spaced apart from both the first spray tip and the second spray tip, and activating an air compressor to introduce compressed air into the housing through the third spray tip;
   simultaneously compressing the first syringe including the biological substance and the second syringe including the activator to introduce the biological substance into the housing through the first spray tip and to introduce the activator into the housing through the second spray tip, the biological substance is activated by the activator upon entering the chamber;
   coating the implant seated within the housing with the activated biological substance, which is provided as a spray upon being exposed to the compressed air at the spray head;
   separating the first end of the chamber from the second end of the chamber via the threaded portion; and
   removing the coated implant from the housing.

2. The method of claim 1, further comprising connecting a first plunger of the first syringe to a second plunger of the second syringe to simultaneously compress the syringes.

3. The method of claim 1, wherein the implant is coated with the activated biological substance outside a sterile operating room field by a non-sterile person and the chamber is separated by the non-sterile person, wherein the implant is removed from the housing by a sterile person.

4. The method of claim 1, further comprising coating a mesh implant sitting atop a support surface spaced from the second end of the housing with the activated biological substance.

5. The method of claim 4, further comprising delivering the activated biological substance through the mesh implant and through the support surface having a plurality of openings to permit passage of the activated biological material therethrough to coat a first surface of the mesh implant.

6. The method of claim 4, further comprising delivering the activated biological substance through the mesh implant to permit passage of the activated biological material therethrough to coat a first surface and a second lower surface.

7. The method of claim 1, further comprising providing the housing with the implant positioned within the chamber in a sterile condition.

8. A method for sterilely spraying a biological substance onto an implant comprising:
   delivering a biological substance through a first spray tip into a chamber of a housing having a first portion and a second portion and housing the implant, the first portion separable from the second portion via a threaded portion;
   delivering an activator of the biological substance through a second spray tip into the chamber;
   delivering compressed air through a third spray tip into the chamber;
   coating the implant that is seated within the housing with the activated biological substance, which is provided as a spray upon being exposed to the compressed air; and
   separating the first portion from the second portion by unthreading the first portion of the housing relative to the second portion via the threaded portion of the housing to expose the implant.

9. The method of claim 8, wherein delivering the biological substance includes connecting a first syringe having the biological substance to a first connector that is in communication with the first spray tip and connecting a second syringe having the activator of the biological substance to a second connector in communication with the second spray tip.

10. The method of claim 8, wherein delivering compressed air further includes connecting an air compressor line to a third connector in communication with the third spray tip to introduce the compressed air into the housing.

11. The method of claim 8, wherein delivering the biological substance and delivering the activator of the biological substance occurs simultaneously.

12. The method of claim 8, wherein the implant is coated with the activated biological substance outside a sterile operating room field by a non-sterile person and the first portion is separated from the second portion by the non-sterile person, the method further comprising removing the implant from within the housing by a sterile person.

13. The method of claim 8, wherein coating the implant further includes coating a mesh implant positioned on a support surface spaced away from an end of the housing.

14. The method of claim 13, further comprising applying the activated biological material through the mesh implant and through openings in the support surface.

15. A method for sterilely spraying a biological substance onto an implant comprising:
- connecting a first source of the biological substance to a housing defining a chamber housing the implant, the chamber having a first end, a second end, and a sidewall having a threaded portion, the sidewall extending between the first end and the second end;
- connecting a second source of an activator of the biological substance to the housing;
- connecting a source of compressed air to the housing to deliver the compressed air into the housing;
- simultaneously delivering the biological substance and the activator into the housing to activate the biological substance;
- coating the implant seated within the housing with the activated biological substance;
- separating the first end of the chamber from the second end of the chamber via the threaded portion; and
- removing the coated implant from the housing.

16. The method of claim 15, further comprising removing the coated implant from the housing by separating a first portion of the housing from a second portion of the housing.

17. The method of claim 15, wherein connecting the first source and the second source to the housing includes connecting a first syringe and a second syringe to the housing, respectively.

18. The method of claim 15, wherein coating the implant further includes coating the implant positioned atop a support surface spaced apart from an end of the housing.

19. The method of claim 15, wherein coating the implant with the activated biological substance occurs outside a sterile operating room field by a non-sterile person, and separating the first end from the second end is done by the non-sterile person, wherein removing the implant from within the housing is done by a sterile person located inside the sterile operating room field.

* * * * *